United States Patent [19]
Gupta

[11] Patent Number: 4,544,453
[45] Date of Patent: Oct. 1, 1985

[54] STRIPPING OF UNREACTED GLYCOL ETHERS AND ACIDS FROM AN ESTERIFICATION REACTION MIXTURE

[75] Inventor: Vijai P. Gupta, Berwyn, Pa.

[73] Assignee: Atlantic Richfield Company, Los Angeles, Calif.

[21] Appl. No.: 615,393

[22] Filed: May 31, 1984

Related U.S. Application Data

[63] Continuation-in-part of Ser. No. 476,305, Mar. 17, 1983.

[51] Int. Cl.[4] ............... C07C 67/24; C07C 67/48; B01D 3/36
[52] U.S. Cl. ............... 203/44; 203/69; 203/62; 203/68; 203/70; 560/230; 560/240; 560/248; 560/263; 562/608; 568/678
[58] Field of Search ............... 203/53, 44, 42, 92, 203/93, 95–97, 69, DIG. 6, 62, 68, 70; 560/248, 240, 230, 263; 562/608; 568/699, 678; 260/410.6, 408

[56] References Cited

U.S. PATENT DOCUMENTS

| | | | |
|---|---|---|---|
| 2,423,545 | 7/1947 | Aeschbach | 203/69 |
| 3,374,153 | 3/1968 | Naglieri | 203/44 |
| 3,476,798 | 11/1969 | Kunstle et al. | 203/44 |
| 3,923,874 | 12/1975 | Hohenschutz et al. | 560/240 |

*Primary Examiner*—Wilbur Bascomb
*Attorney, Agent, or Firm*—Delbert E. McCaslin

[57] ABSTRACT

An improved method of stripping unreacted alkylene glycol monoalkyl ethers and unreacted monocarboxylic or halogenated monocarboxylic acids from a mixture containing the monocarboxylic acid ester prepared therefrom by acid catalyzed esterification without any significant loss of the product ester. The method involves the injection of water into the distillate during the stripping and is particularly suitable for the recovery of propylene glycol monomethyl ether and acetic acid from esterification reaction mixtures containing a predominate amount of product propylene glycol monomethyl ether acetate. The process allows for removal and recovery or recycle of the ether and acid and the preparation of a higher purity product ester.

11 Claims, 1 Drawing Figure

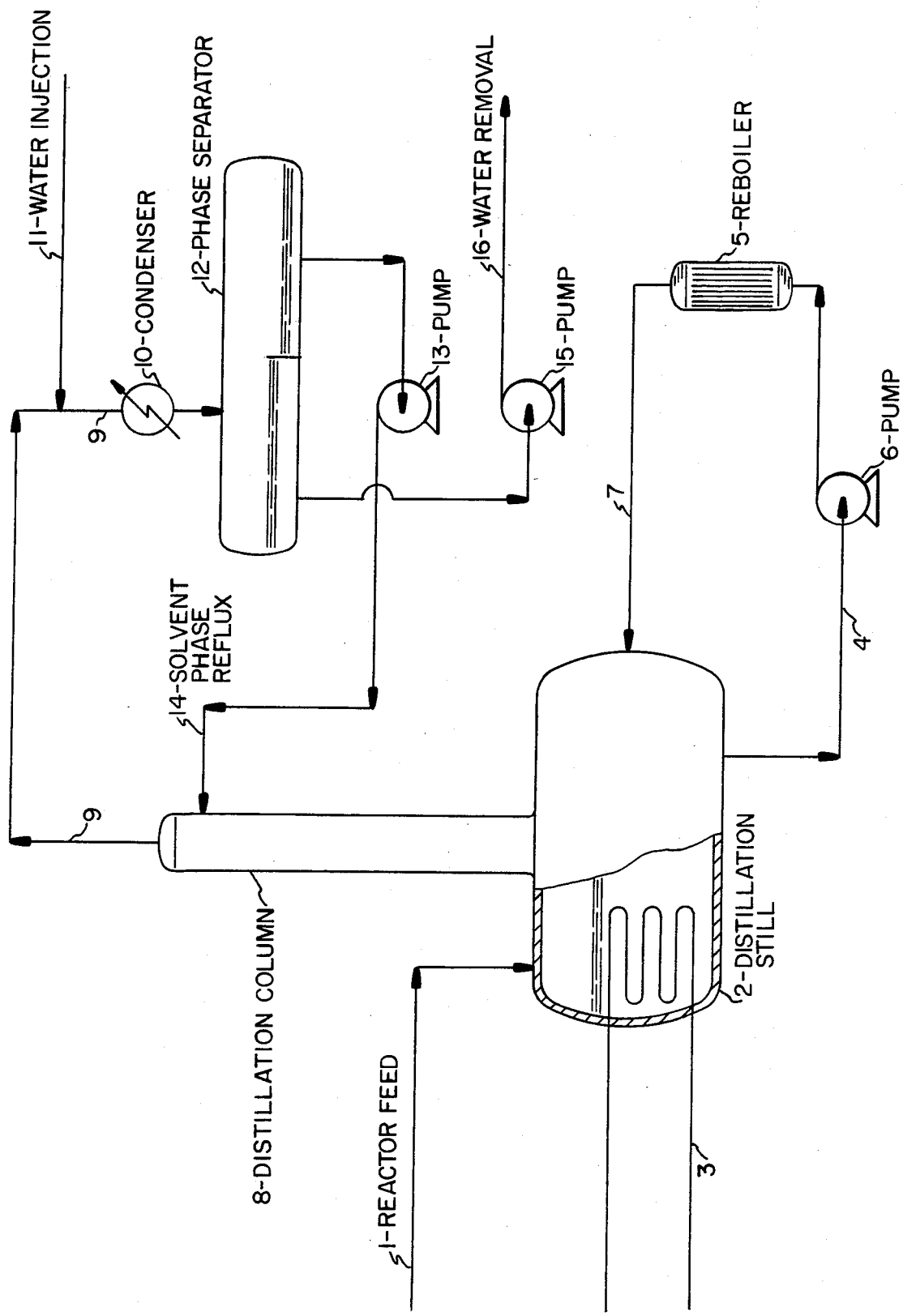

4,544,453

STRIPPING OF UNREACTED GLYCOL ETHERS AND ACIDS FROM AN ESTERIFICATION REACTION MIXTURE

CROSS REFERENCE TO RELATED APPLICATIONS

This application is a continuation-in-part application of Vijai P. Gupta application Ser. No. 476,305, filed Mar. 17, 1983 entitled PREPARATION OF CARBOXYLIC ACID ESTERS OF ALKYLENE GLYCOL MONOALKYL ETHERS which application discloses certain aspects of the present invention.

BACKGROUND OF THE INVENTION

In the above co-pending application of Vijai P. Gupta, Ser. No. 476,305 which application is incorporated herein by reference there is described and claimed a method for the preparation of monocarboxylic acid esters of an alkylene glycol monoalkyl ether which comprises reacting at a pot temperature of from about 80° C. to 165° C. a monocarboxylic or halogenated monocarboxylic acid having from 1 to 10 carbon atoms with an alkylene glycol monoalkyl ether having the formulae $R(OCH_2CHR')_nOH$ and

wherein R is a straight or branched chain alkyl group containing from 1 to 10 carbon atoms, R' is hydrogen or a methyl group and n is an integer of from 1 to 3, in the presence of an acid catalyst and a water-azeotroping solvent which forms a binary minimum-boiling azeotrope with water within the reaction temperature range. Water is removed via a distillation column during the reaction by azeotropic distillation with the water-azeotroping solvent and the solvent phase and water phase are separated and the solvent phase along with a portion of the water phase returned and refluxed to the overhead section of the distillation column. The desired monocarboxylic acid ester is then recovered and may be used as solvents for inks and coating polymers and in cleansers.

In the preparation of the monocarboxylic acid esters the acid is reacted with an alkylene glycol monoalkyl ether generally in the presence of an inert azeotroping solvent such as toluene with an acid catalyst such as paratoluenesulfonic acid. After about 80 to 95% of the glycol ether and monocarboxylic acid have reacted, the rate of further reaction becomes so low because of equilibrium limitations that the reaction is terminated and the unreacted alkylene glycol monoalkyl ether and monocarboxylic acid, which would be present at between about 10% to 2.5% each in the monocarboxylic acid ester product, are stripped out by distillation. Lower conversion mixtures, e.g. 50% ester, which would, for example, contain 25% monocarboxylic acid and 25% glycol ether, may also be concentrated to an 80-95% ester containing range by a straight distillation prior to employment of the water injection method of the present invention.

The present invention relates to the stripping step and provides a novel method of injecting water into the distillate to provide for a separation and refluxing of an azeotropic solvent to the distillation column during stripping to improve the separation of the unreacted ether and acid reactants.

Applicant is not aware of any truly pertinent prior art that is deemed to be anticipatory or suggestive of the concept of the present invention.

SUMMARY OF THE INVENTION

This invention relates to a novel method of stripping by azeotropic distillation unreacted alkylene glycol monoalkyl ethers and unreacted monocarboxylic or halogenated monocarboxylic acids which are contained in the reaction mixture resulting from an acid catalyzed esterification reaction for the preparation of an alkylene glycol monoalkyl ether ester such as propylene glycol monomethyl ether acetate.

It is therefore an object of this invention to provide an improved method for the preparation of monocarboxylic acid esters of glycol ethers in high yield and purity.

It is another object of this invention to provide a method for stripping unreacted acid and ether from the esterification reaction product for reuse or recycle without significant loss of ester product.

These and other objects and advantages of this invention will become apparent from the description and from the claims.

BRIEF DESCRIPTION OF THE DRAWING

The FIGURE is a schematic diagram of a specific flow system which can be used to carry out the process of this invention.

DETAILED DESCRIPTION OF THE INVENTION AND DRAWING

In accordance with the present invention, unreacted monocarboxylic acids and unreacted alkylene glycol monoalkyl ethers which have been utilized in the preparation of an alkylene glycol monoalkyl ether ester and remain in admixture therewith are stripped by azeotropic distillation from the esterification reaction mixture using inert azeotroping solvents while injecting water into the vaporous distillate in order to provide for a separation and refluxing of the azeotropic solvent to the distillation column during the stripping to improve the removal of the monocarboxylic acid and glycol ether and thus provide higher purity ester product.

The stripping of the unreacted acids and ethers may be carried out in the same equipment which was utilized for the catalyzed esterification reaction or other suitable distillation equipment which is equipped with a means for regulating temperature and a means, such as a distillation column, means for the injection of water into the distillate vapor, a condenser and a phase separator or decanter, for removal of the solvent-acid-ether azeotrope and a means for returning the azeotroping solvent to the distillation column. A general procedure for carrying out the stripping method is to heat the distillation pot or still containing the alkylene glycol monoalkyl ether ester product, unreacted monocarboxylic acid and alkylene glycol monoalkyl ether, a small amount of esterification catalyst and an inert azeotroping solvent to the desired temperature for an appropriate time while azeotroping off the unreacted acid and ether and injecting water into the distillate vapor which is condensed and sent to a phase separator. The azeotroping solvent is returned as reflux and the water containing the unreacted acid and ether is removed for further processing.

The water which is injected into the distillate to extract the monocarboxylic acid and glycol ether may be from any source, i.e., fresh water or water which may be reclaimed from the glycol ether-carboxylic acid reaction to prepare the ester as described in the above mentioned Gupta application Ser. No. 476,305.

The unreacted alkylene glycol monoalkyl ethers which are stripped, according to the present method, from the esterification reaction mixture conform to the general formula R(OCH$_2$CHR')$_n$OH and the isomer

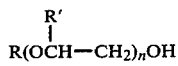

may be prepared for example by the process disclosed in U.S. Pat. Nos. 2,816,932 and 4,299,997. Representative alkylene glycol monoalkyl ethers within the above noted formula and suitable for use in this invention include, for example, ethylene glycol and diethylene glycol monomethyl, -ethyl, -propyl, -isopropyl, -butyl, -tertiary-butyl, -isobutyl, -amyl, -hexyl, -octyl, -decyl, etc., ethers, propylene glycol, dipropylene glycol and tripropylene glycol mono-methyl, -ethyl, -propyl, -isopropyl, -butyl, -amyl, -octyl, -decyl, etc., ethers.

The monocarboxylic acid which are employed as reactants in the esterification reaction and are removed according to the present invention include monocarboxylic and halogenated monocarboxylic acids having from 1 to 10 carbon atoms. Representative monocarboxylic acids include for example, formic, acetic, propionic, n-butyric, isobutyric, caproic, trimethylacetic, chloroacetic, bromoacetic, chloroproponic, etc., acids.

The inert azeotroping solvents for use in the process of this invention include those solvents forming a binary minimum-boiling azeotrope with the monocarboxylic acids and glycol ethers at a distillation temperature range of from about 50° C. to 150° C. at atmospheric or subatmospheric pressure. Representative azeotroping solvents include, for example, aromatic hydrocarbons such as benzene, toluene, xylene, chlorobenzene, bromobenzene, alkanes and cycloalkanes such as n-pentane, trimethylpentane, isopentane, n-hexane, n-heptane, nonane, 3,4-dimethylhexane, 3-ethylhexane, cyclohexane, methyl cyclohexane, cyclopentane, cyclooctane, halogenated aliphatic compounds such as chloroform, carbon tetrachloride, 1,2-dichloroethane, trichloroethane, etc., as well as diethylketone. Toluene is the preferred solvent. The solvent employed in the esterification reaction will generally also be used to strip the unreacted acid and ether according to the present invention.

The still or pot temperature for the stripping method of the present invention may range between about 50° C. and 150° C. and is preferably between 95° C. and 120° C. Still or pot temperatures will of course be based on the azeotroping solvent and pressure, if any, employed. The glycol ether and acid are preferably stripped under vacuum. Pressures of from about 20 mm Hg up to about 760 mm Hg and preferably from 200 mm Hg to 500 mm Hg may be employed.

While the inert azeotroping solvent improves the separation of the monocarboxylic acid and glycol ether from the glycol ether ester, if used alone it does not phase separate and would therefore be removed from the system with the condensed distillate since the solvent could not be refluxed or recycled. In the circumstance, a continuous make up of solvent resulting in a large volume inventory of solvent would be necessary.

The present invention involving water injection solves this problem and further reduces product glycol ether ester losses. The glycol ether and monocarboxylic acid are miscible with water and can be removed from the solvent phase containing same by extraction with the water injected into the distillate. Any glycol ether ester product, which may be carried over with the distillate, has limited solubility in water and cannot be effectively removed from the solvent phase by water extraction and is refluxed to the distillation column. Thus the method of the present invention uses azeotroping solvent to improve the separation of the unreacted glycol ether and carboxylic acid and utilizes water to extract out these unreacted components, allowing the azeotroping solvent to be returned as reflux which eliminates any need for a continuous makeup of solvent.

The water injection rate into the distillate prior to condensation and removal will be at least 5% by weight of the distillate vapor and is preferably injected at a rate of between about 50% to 300% by weight of the distillate vapor. Obviously there is no upper limit to the amount of water injected and removed, but from a practical and operational stand point, larger amounts provide no apparent improvement in results and accordingly, would only necessitate the burdensome handling of large volumes of water to remove and/or recover the unreacted monocarboxylic acid and glycol ethers. Water could be injected into the top of the distillation column but is preferably injected into the distillation column vapor line, i.e. upstream of the consenser (as shown in the drawing) to avoid any increase in heat load on the distillation column heating system.

Depending on the amount of conversion of reactants, the final esterification reaction product mixture may vary in the amount of ester product, unreacted acid and ether reactants, solvent and water content contained therein. Typically a reaction product mixture, after the esterification reaction is about 87% alkylene glycol monoalkyl ether ester, 5% alkylene glycol monoalkyl ether, 5% monocarboxylic acid, 2 to 5% solvent, 0.5% acid catalyst such as para-toluene sulfonic acid and a trace of water.

In order to describe the invention in greater detail, reference is made to the drawing wherein an azeotroping solvent is fed via line 1 to distillation still 2 which contains a reaction product mixture resulting from the preparation, in the same process equipment, of a monocarboxylic acid ester of an alkylene glycol monoalkyl ether such as for example, propylene glycol monomethyl ether acetate by the acid catalyzed esterification of acetic acid with propylene glycol monomethyl ether. A reaction product mixture which has been prepared in a separate reactor section may also be fed to the distillation still via line 1 along with the azeotroping solvent. The distillation still is then heated to distillation temperatures by heating coils 3 within the still or by recirculation of the reaction mixture through line 4 via pump 6 to reboiler 5 and through line 7 back into the distillation still. Azeotroping solvent, unreacted glycol ether and monocarboxylic acid as well as small amounts of ester product pass into distillation column 8 which is maintained under vacuuum. A predominantly ether and acid solvent azeotrope is taken off the top of the distillation 8 via line 9 to condenser 10. Water is injected into line 9 upstream of condenser 10 to extract the unreacted ether and acid. The condenser water with the ether and acid and the solvent are then fed to phase separator 12.

The azeotroping solvent and water-ether-acid mixture are separated in phase separator 12. The azeotroping solvent and water-ether-acid mixture are separated in phase separator 12. The solvent phase is then removed and refluxed to the distillation column 8 via pump 13 and line 14 while the water-ether-acid phase is removed via pump 15 through line 16 for recovery or recycle of the ether and acid.

Although the method of the present invention will be directed principally to the preparation of the acetic acid ester of propylene glycol monomethyl ether and dipropylene glycol monomethyl ether it is not intended that the method be limited to such ester preparation and those skilled in the art will recognize that the present method is broadly applicable to the preparation of other esters such as propylene glycol monobutyl acetate, dipropylene monooctyl butyrate, ethylene glycol monoethyl formate, etc., using the appropriate glycol ether and monocarboxylic acid.

The following examples are provided to illustrate the invention in accordance with the principles of this invention but are not to be construed as limiting the invention in anyway except as indicated by the appended claims.

EXAMPLE 1 (Comparative)

A straight batch distillation employing a 20 tray Oldershaw column at a reflux ratio of 10/1 at atmospheric pressure with a pot temperature of 140°–146° C. and an overhead temperature of 115°–140° C. was carried out on a reaction mixture resulting from an acid catalyzed esterification of propylene glycol monomethyl ether (PM) and acetic acid to produce propylene glycol monomethyl acetate (PMA). The reaction mixture contained on a percent by weight basis 97.2% propylene glycol monomethyl ether acetate, 2.0% unreacted acetic acid, 0.1% unreacted propylene glycol monomethyl ether and 0.7% p-toluene sulfonic acid catalyst. The distillation was carried out for 1 hour and a 14% overhead cut taken. The results were as follows:

|  | Charge % | Overhead % | Bottoms % |
|---|---|---|---|
| PMA | 97.2 | 89.1 | 98.7 |
| Acetic Acid | 2.0 | 10.9 | 0.6 |
| PM | 0.1 | 0.6 | none |
| p-toluenesulfonic acid catalyst | 0.7 | none | 0.7 |

13% of the propylene glycol monomethyl ether acetate product (PMA) was taken overhead and the bottoms product was still at 0.6%.

EXAMPLE 2 (Comparative)

The procedure of Example 1 was repeated. The same equipment was employed except that toluene was continuously added to the still pot at a reflux ratio of 10/1 at atmospheric pressure, an overhead temperature of 104° C.–105° C. and a bottoms temperature of 140° C. The still pot contained on a % by weight basis, 97.5% propylene glycol monomethyl ether acetate (PMA), 1.8% acetic acid, 0.6% p-toluenesulfonic acid and a trace of propylene glycol monomethyl ether. The distillation was carried out for 4 hours. The results were as follows:

| Toluene Added % of Initial Charge | Accumulative Overhead Composition | | % Acetic Acid in Bottoms | Cumulative % of PMA Charge in Toluene |
|---|---|---|---|---|
| | PMA | Acetic | | |
| 7.7 | 18.3 | 39.3 | 0.33 | 3.1 |
| 14.9 | 10.7 | 26.7 | 0.14 | 4.0 |
| 21.9 | 7.7 | 20.1 | 0.05 | 4.5 |

The acetic acid content of the product bottoms was reduced to less than 0.1% with a solvent feed of 22% of the reactor charge.

EXAMPLES 3–4

The procedure of Example 1 was repeated except that 7% by weight toluene was added to the pot and water was injected into the vaporous distillate at a rate of 1 cc and 2 cc/min. The distillate was phase separated with Dean Stark apparatus. The toluene solvent phase was refluxed to the column and the water phase containing unreacted acetic acid and a trace of propylene glycol monomethyl ether was removed. No propylene glycol monomethyl ether acetate product was in the water phase. In both Examples 3 and 4 the distillation pot charge contained on a percent by weight basis, 97.7% PMA, 1.56% acetic acid, 0.7% p-toluenesulfonic acid and a trace amount of propylene glycol monomethyl ether. The results of Example 3 (water injection at 1 cc/minute were as follows:

| | Overhead Composition Water Phase % Acetic Acid | Pot Composition % Acetic Acid |
|---|---|---|
| EXAMPLE 3 | | |
| Water Injection 1 cc/min. | | |
| 4.9 | 14.0 | 0.90 |
| 10.0 | 10.6 | 0.51 |
| 15.0 | 8.6 | 0.28 |
| 21.0 | 6.8 | 0.13 |
| EXAMPLE 4 | | |
| Water Injection 2 cc/min. | | |
| 21.4 | 6.6 | 0.17 |
| 33.0 | 5.4 | 0.05 |

EXAMPLE 5

The procedure of Example 3 and 4 was repeated with the injection of water into the overhead vaporous distillate and a solvent reflux. A 30 tray Oldershaw was employed using Dean Stark Apparatus to phase separate the toluene solvent and water. The water which was injected to extract the acetic acid and glycol ether from the distillate was recycled water and contained 6 weight percent acetic acid and 12 weight percent propylene glycol monomethyl ether. The charge to the distillation pot which resulted from an acid catalyzed esterification reaction contained 84% by wt. propylene glycol monomethyl ether acetate product (PMA), 5.0% by wt. unreacted acetic acid, 6.0% by wt. unreacted propylene glycol monomethyl ether (PM), 0.3% by wt. p-toluene sulfonic acid catalyst and 5.0% by wt. added toluene azeotroping solvent. The stripping distillation was run for 5, 12 and 24 hours at a pressure of 200 mm Hg. with a pot temperature of 108° C. and an overhead temperature of 68° C. The results are as follows:

| Distillation Pot Composition | | |
| --- | --- | --- |
| Hours of Stripping | % Total Acid (includes catalyst) | % PM |
| 0 | 5.1 | 6.0 |
| 5 | 3.2 | 1.2 |
| 12 | 2.1 | trace |
| 24 | 0.5 | trace |

We claim:

1. A method for the removal of unreacted alkylene glycol monoalkyl ether and unreacted monocarboxylic acid from an acid catalyzed esterification reaction product mixture containing said glycol ether and acid along with a predominant amount of the monocarboxylic acid ester of the alkylene glycol monoalkyl ether and produced by said esterification which comprises the steps of:

distilling at a temperature of from about 50° C. to 150° C. said esterification reaction product mixture in the presence of an inert azeotroping solvent to remove via a distillation column unreacted monocarboxylic acid and unreacted alkylene glycol monoalkyl ether from the reaction product mixture as a vaporous distillate;

injecting water into the vaporous distillate containing the monocarboxylic acid, glycol ether and solvent azeotrope;

condensing the distillate containing the water forming a solvent phase and a water phase which extracts and contains the monocarboxylic acid and unreacted glycol ether;

returning and refluxing the solvent phase to the overhead section of the distillation column; and removing the water phase containing the unreacted alkylene glycol monoalkyl ether and unreacted monocarboxylic acid.

2. A method according to claim 1 wherein the monocarboxylic acid is acetic acid.

3. A method according to claim 1 wherein the alkylene glycol monoalkyl ether is propylene glycol monomethyl ether.

4. A method according to claim 1 wherein the distillation temperature is between 95° C. and 120° C.

5. A method according to claim 1 wherein the azeotroping solvent is toluene.

6. A method according to claim 1 wherein at least about 5 weight percent water is injected based on the vaporous distillate.

7. A method according to claim 6 wherein between 50 and 300 weight percent water is injected.

8. A method according to claim 1 wherein the reaction is carried out under a pressure of from about 20 mm Hg to 760 mm Hg.

9. A method according to claim 8 wherein the pressure is between 200 mm Hg and 500 mm Hg.

10. A method according to claim 1 wherein the esterification reaction product mixture consists essentially of propylene glycol monomethyl ether acetate along with unreacted acetic acid and unreacted propylene glycol monomethyl ether.

11. A method for the removal of unreacted propylene glycol monomethyl ether and unreacted acetic acid from an acid catalyzed esterification reaction product mixture containing said glycol ether and acetic acid along with a predominant amount of the propylene glycol monomethyl ether acetate produced by said esterification which comprises the steps of:

distilling at a temperature of from 95° C. to 120° C. said esterification reaction product mixture in the presence of toluene azeotroping solvent to remove via a distillation column the unreacted propylene glycol monomethyl ether and acetic acid from the product mixture as a vaporous distillate;

injecting water into the vaporous distillate containing the glycol ether, acetic acid and solvent;

condensing the distillate containing the water forming a solvent phase and a water phase which extracts and contains unreacted glycol ether and acetic acid;

returning and refluxing the solvent phase to the overhead section of the distillation column; and removing the water phase containing unreacted propylene glycol monomethyl ether and unreacted acetic acid.

\* \* \* \* \*